US008609355B2

(12) United States Patent
Swiss et al.

(10) Patent No.: US 8,609,355 B2
(45) Date of Patent: Dec. 17, 2013

(54) ASSAYS FOR THE DETECTION OF MICROBES

(75) Inventors: Gerald F. Swiss, Rancho Santa Fe, CA (US); Laurie B. F. Stellman, Union City, CA (US)

(73) Assignee: Indicator Systems International, Inc., Newport Beach, CA (US)

( * ) Notice: Subject to any disclaimer, the term of this patent is extended or adjusted under 35 U.S.C. 154(b) by 0 days.

(21) Appl. No.: 13/558,127

(22) Filed: Jul. 25, 2012

(65) Prior Publication Data

US 2013/0029349 A1 Jan. 31, 2013

Related U.S. Application Data

(60) Provisional application No. 61/511,914, filed on Jul. 26, 2011.

(51) Int. Cl.
*G01N 33/544* (2006.01)

(52) U.S. Cl.
USPC .......... 435/7.32; 436/518; 436/808; 436/811; 436/164; 436/163; 436/805; 435/975; 422/400; 422/430

(58) Field of Classification Search
None
See application file for complete search history.

(56) References Cited

U.S. PATENT DOCUMENTS

| | | | |
|---|---|---|---|
| 3,645,852 A | 2/1972 | Axen et al. | |
| 3,720,760 A | 3/1973 | Bennich et al. | |
| 4,704,692 A | 11/1987 | Ladner | |
| 5,191,066 A | 3/1993 | Bieniarz et al. | |
| 5,350,674 A | 9/1994 | Boenisch et al. | |
| 5,627,052 A | 5/1997 | Schrader | |
| 5,670,153 A | 9/1997 | Weiner et al. | |
| 5,686,073 A | 11/1997 | Campbell et al. | |
| 5,723,323 A | 3/1998 | Kauffman et al. | |
| 5,763,192 A | 6/1998 | Kauffman et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,976,862 A | 11/1999 | Kauffman et al. | |
| 6,322,788 B1 | 11/2001 | Kim | |
| 6,656,746 B2 | 12/2003 | Sprecher et al. | |
| 6,709,659 B1 | 3/2004 | Lok et al. | |
| 7,060,800 B2 | 6/2006 | Gorman | |
| 7,119,179 B1 | 10/2006 | Huynh et al. | |
| 7,279,559 B2 | 10/2007 | Jacobs et al. | |
| 7,612,020 B2 * | 11/2009 | Stuelpnagel et al. | 506/13 |
| 8,425,996 B2 | 4/2013 | Gorski et al. | |
| 2004/0081588 A1 | 4/2004 | Hammerstedt et al. | |
| 2005/0011206 A1 | 1/2005 | Luo et al. | |
| 2005/0226893 A1 | 10/2005 | Juneau et al. | |
| 2006/0014227 A1 | 1/2006 | Fleming et al. | |
| 2006/0246523 A1 | 11/2006 | Bieniarz et al. | |
| 2009/0181406 A1 | 7/2009 | Ridder et al. | |
| 2010/0129836 A1 | 5/2010 | Goodnow | |
| 2010/0285986 A1 * | 11/2010 | Menges et al. | 506/9 |

FOREIGN PATENT DOCUMENTS

| | | | |
|---|---|---|---|
| WO | WO-03/050556 A2 | | 6/2003 |
| WO | WO-2009-056350 | * | 5/2009 |

OTHER PUBLICATIONS

Moris-Varas et al., Visualization of enzyme-catalyzed reactions using pH indicators: rapid screening of hydrolase libraries and estimation of the enantioselectivity, Oct. 1999, Bioorganic & Medicinal Chemistry 7 pp. 2183-2188.*
Babcook, et al., "A novel strategy for generating monoclonal antibodies from single, isolated lymphocytes producing antibodies of defined specificities," Proc. Natl. Acad. Sci., (1996), 93:7843-7848.
Eren, et al., "Human monoclonal antibodies specific to hepatitis B virus generated in a human/mouse radiation chimera: the Trimera system," Immunol., (1998), 93:154-161.
Gray, et al., "Secretion capture and report web: use of affinity derivatized agarose microdroplets for the selection of hybridoma cells," J. Immunol. Methods, (1995), 182(2):155-163.
Hanes, et al., "In vitro selection and evolution of functional proteins by using ribosome display," Proc. Natl. Acad. Sci., (1997), 94:4937-4942.
Hanes, et al., "Ribosome display efficiently selects and evolves high-affinity antibodies in vitro from immune libraries," Proc. Natl. Acad. Sci., (1998), 95:14130-14135.
Kapetanovic, I.M., "Computer-aided drug discovery and development (CADDD): in silico-chemico-biological approach," Chem. Biol. Interact., (2008), 171(2):165-176.
Kenney, et al., "Production of monoclonal antibodies using a secretion capture report web," Biotechnology, (1995), 13(8):787-790.
Nguyen, et al., "Production of human monoclonal antibodies in SCID mouse," Microbiol. Immunol., (1997), 41(12):901-907.
PCT International Search Report and Written Opinion dated Feb. 22, 2013 in related PCT Application No. PCT/US2012/048186.
Powell, et al., "Gel microdroplets and flow cytometry: Rapid determination of antibody secretion by individual cells within a cell population," Biotechnology, (1990), 8(4):333-337.
Rotmans, et al., "Cross-linking of Schistosoma mansoni antigens and their covalent binding on the surface of polystyrene microtitration trays for use in the ELISA," J. Immunol. Methods, (1983), 57(1-3):87-98.
Sandhu, et al., "The use of SCID mice in biotechnology and as a model for human disease," Crit. Rev. Biotechnol., (1996), 16(1):95-118.
Steenbakkers, et al., "Efficient generation of monoclonal antibodies from preselected antigen-specific B cells. Efficient immortalization of preselected B cells," Mol. Biol. Rep., (1994), 19(2):125-134.
Wen, et al., "Limiting dilution assay for human B cells based on their activation by mutant EL4 thymoma cells: total and antimalaria responder B cell frequencies," Eur. J. Immunol., (1987), 17(6):887-892.

* cited by examiner

*Primary Examiner* — Chris L Chin
*Assistant Examiner* — Scott Black
(74) *Attorney, Agent, or Firm* — Foley & Lardner LLP

(57) ABSTRACT

Methods, devices, and kits are provided herein for the accurate and rapid detection of disease causing microbes in a sample by the detection of microbial components of which correlate to the presence of the microbe. Kits include a first binding agent operatively coupled to an immobilized support; and a second binding agent operatively coupled to one or more pH indicating moieties wherein the first and second binding agents bind with sufficient specificity to the microbial component to permit detection of that component which correlates to the presence of the microbe in the sample.

17 Claims, No Drawings

ASSAYS FOR THE DETECTION OF MICROBES

CROSS-REFERENCE TO RELATED APPLICATIONS

This application claims the benefit under 35 U.S.C. §119 (e) to U.S. provisional Application Ser. No. 61/511,914, filed Jul. 26, 2011, which is hereby incorporated by reference into this application in its entirety.

TECHNICAL FIELD

This invention relates to assays which, in a preferred embodiment, permits the rapid and accurate detection of antigens such as microbes, toxins and other components in a sample.

BACKGROUND

Early detection of the presence of microbes, toxins or other components in food and/or water or the early detection of infection is a long desired goal in preventing human diseases. For example, cholera continues to be a major public health concern in developing countries. The disease is a toxin-mediated bacterial infection, caused by certain serogroups of *Vibrio cholerae*, that has the ability to cause outbreaks of epidemic proportions. In the last 200 years there have been at least 7 cholera pandemics, of which the latest still continues.

The current pandemic, which began in 1961 in Indonesia, has now circled the globe, affecting countries in Asia, Africa, Europe and South America. In 2003 outbreaks were reported in many countries, including South Africa, Mozambique, the Democratic Republic of the Congo, Liberia and Iraq.

Similarly, malaria is another major health issue in developing countries especially in tropical Africa and Asia. While malaria is curable, efficacious treatment requires early diagnosis and prompt treatment. Conventionally, the presence of malaria in a patient correlates to the presence of the malarial enzyme pGluDH (Glutamate dehydrogenase) or lactate dehydrogenase which is not present in human blood cells.

Current diagnostic tests for such diseases can be relatively expensive and may require the aid of a skilled technician to interpret such tests. These limitations pose challenges to using these tests in developing countries where they are needed the most.

As outbreaks of these and other diseases due to microbial toxins or the microbes themselves occur in developing or third-world countries. There the accurate diagnosis of such diseases remains a challenge due to lack of resources such as the availability of equipment typically used for detection in routine assays. In addition to such cost concerns, challenges in the detection of disease faced by individuals in these regions of the world also include the lack of trained individuals to properly use and evaluate the results provided by the detection instrumentation.

Thus, there is a need in the art for diagnostic assays that allow for rapid and accurate detection of microbial mediated diseases. Furthermore, there is also a need for assays that, in general, are easy to use and easy to interpret regardless of the technical skill of the individual performing the assay.

SUMMARY OF THE INVENTION

Described herein are assays which employ pH indicators to facilitate rapid and accurate evaluation of the assay results. In one embodiment, these assays are useful for the detection of microbial diseases either by detection of microbial components which correlate to the disease causing microbe in samples such as bodily fluids, bodily wastes, liquids such as water or samples which may be suspected to contain the disease causing microbes.

In one aspect, this invention relates to a kit for the accurate and rapid detection of disease causing microbes in a sample by the detection of microbial components which correlate to the presence of the microbe. The kit comprises a first binding agent operatively coupled to an immobilized support; and a second binding agent operatively coupled to one or more pH indicating moieties wherein the first and second binding agents bind with sufficient specificity to the microbial component to permit detection of that component which correlates to the presence of the microbe in the sample.

In another aspect, this invention provides for a device for the accurate and rapid detection of a microbial component which correlates to the presence of a disease causing microbe in a sample comprising an assay device having one or more assay compartments wherein each assay compartment comprises: a first binding agent operatively coupled to an immobilized support; and a second binding agent operatively coupled to one or more pH indicating moieties wherein the first and second binding agents bind with sufficient specificity to the microbial component to permit detection of the microbe in the sample and further wherein the second binding agent is not operatively coupled to the immobilized support to which the first binding agent is bound.

In one of its method aspects there is provided a method for accurately and rapidly detecting the presence or absence of microbial components in a sample said method comprising:

providing an assay device having an assay compartment for conducting the assay wherein said assay compartment comprises a first binding agent operatively coupled to an immobilized support; and a second binding agent operatively coupled to one or more pH indicating moieties wherein the first and second binding agents bind with sufficient specificity to a microbial component so as to permit detection of the microbe in the sample and further wherein the second binding agent is not operatively coupled to the immobilized support to which the first binding agent is bound;

adding the sample to the assay compartment of the assay device;

incubating the assay compartment under conditions sufficient to permit binding of the first and second binding agent to at least a portion of any microbial component present;

washing the assay compartment one or more times with a first inert solution under conditions which remove any of the second binding agent not bound to the microbial component;

adding a second inert solution wherein the pH of the second inert solution is one which allows the visible detection of the presence or absence of pH indicating moities in the assay;

and correlating the color or lack thereof with the presence or absence of a microbial component in a sample.

The methods described herein can be modified as necessary to be useful in what are otherwise conventional assays. For example, a competitive assay may use a limited amount of receptor, preferably operatively coupled to a solid support within the assay compartment. It may also use a limited amount of a ligand to that receptor having operatively coupled thereto one or more pH indicators (Ligand A).

Into the assay compartment is mixed a sample suspected of containing the same ligand as Ligand A albeit without any pH indicator operatively coupled thereto (Ligand B). In one embodiment, if present, the number of Ligand B suspected in the sample will exceed and, preferably, greatly exceed, the number of receptors. When incubated as per the above, if Ligand B is not in the sample, only Ligand A will bind to the receptor and upon a change in pH, the assay compartment will change colors indicating the lack of the disease causing microbe. Contrarily, if Ligand B is in the sample at an amount sufficient to cause the disease, the significantly greater population of Ligand B will cause most of Ligand A to be released from the receptor. In such a case, the assay compartment will not change colors but the eluent from this assay will.

Accordingly, this invention can be used with any conventional assay wherein the assay uses a change in or initiation of a detectable signal as a basis to determine the presence of an analyte (such as a component of a disease causing microbe) or the confirmation of the occurrence of a biological event. In some embodiments, the presence of a disease causing microbe can be determined the assessing the presence of the microbe or a component thereof such as the toxin produced or an enzyme specific for that microbe.

As such, there is provided an improved method for conducting assays wherein the presence or absence of an analyte in a sample suspected of containing the analyte or the occurrence of a biological event is determined by measuring a detectable signal which correlates to the presence or absence of the analyte in the sample or the occurrence of a biological event wherein the improvement comprises employing a pH indicator as the detectable signal. In one embodiment, the detectable signal produced by the pH indicator is a change from a clear solution at physiological pH to a colored solution at more acidic and typically non-physiological pH in the presence of the analyte or the occurrence of a biological event. In another embodiment, the detectable signal produced by the pH indicator is a change from a colored solution at physiological pH to a clear solution at non-physiological pH in the presence of the analyte or the occurrence of a biological event. In yet another embodiment, the detectable signal produced by the pH indicator is a change from a first colored solution at physiological pH to a second colored solution at non-physiological pH in the presence of the analyte or the occurrence of a biological event.

In one embodiment, the analyte is either a microbial toxin or an enzyme produced by the microbe which is specific to that microbe. In another preferred embodiment, the analyte is a medicinal drug.

Still further, there are assays which use a change in a detectable signal to assess endocytosis of a particle such as a liposome into a targeted cell. US Patent Application Publication No. 2005/0112065, which is incorporated herein by reference in its entirety, discloses remote detection of endocytosis by liposomes comprising a detectable marker, such as a paramagnetic metal chelate or fluorescent marker, due to the pH change when the liposomes enter the cells. The pH indicators described herein can be used with liposomes in such a setting wherein an in vitro assay would indicate endocytosis merely by a color change. Accordingly, this invention allows for the in vitro detection of a biological event that can be correlated to in vivo utility. In such a method, a component of the biological event is coupled to a pH indicator and the location of the pH indicator after the biological event should have transpired can be readily detected by pH change. In some events, the pH change occurs endogenously and in some events occurs by the addition of a pH buffer. As necessary, a bright field, deconvolution or flourescent microscope capable of detecting emitted and/or absorbed wavelengths can be used to access the presence or absence of color in the endosomes.

DETAILED DESCRIPTION OF THE INVENTION

Throughout this application, the text refers to various embodiments relating to assays, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the instant invention.

DEFINITIONS

As used herein, certain terms may have the following defined meanings. As used in the specification and claims, the singular form "a," "an" and "the" include singular and plural references unless the context clearly dictates otherwise.

The term "comprising" is intended to mean that the compounds and methods include the recited elements, but not excluding others. "Consisting essentially of" when used to define compositions and methods, shall mean excluding other elements of any essential significance to the compounds or methods. "Consisting of" shall mean excluding more than trace elements of other ingredients for claimed compounds and substantial method steps. Embodiments defined by each of these transitional terms are within the scope of this invention. Accordingly, it is intended that the processes and compositions can include additional steps and components (comprising) or alternatively include additional steps and compounds of no significance (consisting essentially of) or alternatively, intending only the stated methods steps or compounds (consisting of).

Neutral pH has a value of 7.0. As used herein, the term "neutral pH" also includes low acid pH of from about 6 to below 7 and low basic pH of from above 7 to up to about 8. "Physiological pH" refers to a pH of from approximately 6.7 to about 7.3.

The term "indicator" refers to a substance capable of changing color with a change in pH caused when a threshold amount of bacterial by-products are produced. In one embodiment, the indicator is a pH indicator. Such pH indicators are sometimes referred to herein as "pH indicating moieties."

Examples of pH indicators include xylenol blue (p-xylenolsulfonephthalein), bromocresol purple (5',5"-dibromo-o-cresolsulfonephthalein), bromocresol green (tetrabromo-m-cresolsulfonephthalein), cresol red (o-cresolsulfonephthalein), m-cresol purple, thymol blue, o-cresolphthalein, thymolphthalein, crystal violet, malachite green, phenolphthalein, phenol red, bromothymol blue (3',3"-dibromothymolsulfonephthalein), p-naphtholbenzein (4-[alpha-(4-hydroxy-1-naphthyl)benzylidene]-1(4H)-naphthalenone), neutral red (3-amino-7-dimethylamino-2-methylphenazine chloride), pentamethoxy red, hexamethoxy red and heptamethoxy red, and combinations thereof. In one embodiment, the pH indicators are hexamethoxy red and/or heptamethoxy red or derivatives thereof.

The term "microbial component" is meant to refer to a distinct detectable molecule specific to a microbe such as a bacterium, a fungi, or a virus, for example. The microbial component may be a toxin, an enzyme, or another molecule such as a carbohydrate or lipid. By way of example, toxins produced from microbes include: anthrax toxin, subtilase cytotoxin, pasteurella multocida toxin, vibrio RTX toxins (cholera toxin), helicobacter pylori toxin, staphylococcal toxins, mycotoxins, and fungal ribotoxins. Enzymes specific to microbes include, for example, Glutamate dehydrogenase or Lactate dehydrogenase as in malaria. Other molecules include endotoxin, such as LPS produced by gram negative bacteria. It is required that first and second binding agents that specifically bind said microbial component be included in the assay. In most cases, binding agents with such specificity are known in the art and are commercially available. When there are no known binding agents to the microbial component, binding agents such as antibodies or compounds can be developed by methods known in the art and described herein.

The term "analyte" as used herein is meant to refer to a molecule that can be detected by the assays, methods and devices described herein. An analyte is not restricted to a microbial component but also includes synthetic and natural compounds such as, by way of example only, illicit drugs, drugs, proteins, nucleic acids, environmental pollutants, and peptides. As with a microbial component, it is required that binding agents that specifically bind said analyte be included in the assay. In most cases, binding agents with such specificity are known in the art and are commercially available. When there are no known binding agents to the analyte, binding agents such as antibodies or compounds can be developed by methods known in the art and those described herein. In the case of nucleic acids, binding agents are the complement of the nucleic acid of interest. Methods for isolating and sequencing nucleic acids are well known in the art (See, e.g., Sambrook and Russell eds. (2001) Molecular Cloning: A Laboratory Manual, $3^{rd}$ edition)

Another aspect of this invention relates to a device for the accurate and rapid detection of a microbial component which correlates to the presence of a disease causing microbe in a sample comprising an assay device having one or more assay compartments wherein each assay compartment comprises: a first binding agent operatively coupled to an immobilized support; and a second binding agent operatively coupled to one or more pH indicating moieties wherein the first and second binding agents bind with sufficient specificity to the microbial component to permit detection of the microbe in the sample and further wherein the second binding agent is not operatively coupled to the immobilized support to which the first binding agent is bound.

In one embodiment, the kit and/or device further comprises a pH buffered solution. In a related embodiment, the pH of said buffered solution is one in which said pH indicating moieties are colorful. Solutions can be buffered at a pH of choosing by the selection of an appropriate buffer according to the pKa of the buffer. In a preferred embodiment, the pH buffered solution is inert. The term "inert" as used herein is meant to refer to a solution or composition that does not disrupt the binding reactions and/or molecular interactions in the assay.

Some non-limiting examples of buffers and their properties are included in Table 1 below:

TABLE 1

| Common Name | pKa at 25° C. | Buffer Range | Temp Effect dpH/dT in (1/K) ** | Mol. Weight | Full Compound Name |
|---|---|---|---|---|---|
| TAPS | 8.43 | 7.7-9.1 | −0.018 | 243.3 | 3-{[tris(hydroxymethyl)methyl]amino}propanesulfonic acid |
| Bicine | 8.35 | 7.6-9.0 | −0.018 | 163.2 | N,N-bis(2-hydroxyethyl)glycine |
| Tris | 8.06 | 7.5-9.0 | −0.028 | 121.14 | tris(hydroxymethyl)methylamine |
| Tricine | 8.05 | 7.4-8.8 | −0.021 | 179.2 | N-tris(hydroxymethyl)methylglycine |
| TAPSO | 7.635 | 7.0-8.2 | | 259.3 | 3-[N-Tris(hydroxymethyl)methylamino]-2-hydroxypropanesulfonic Acid |
| HEPES | 7.55 | 6.8-8.2 | −0.014 | 238.3 | 4-2-hydroxyethyl-1-piperazineethanesulfonic acid |
| TES | 7.40 | 6.8-8.2 | −0.020 | 229.20 | 2-{[tris(hydroxymethyl)methyl]amino}ethanesulfonic acid |
| MOPS | 7.20 | 6.5-7.9 | −0.015 | 209.3 | 3-(N-morpholino)propanesulfonic acid |
| PIPES | 6.76 | 6.1-7.5 | −0.008 | 302.4 | piperazine-N,N'-bis(2-ethanesulfonic acid) |
| Cacodylate | 6.27 | 5.0-7.4 | | 138.0 | dimethylarsinic acid |
| SSC | 7.0 | 6.5-7.5 | | 189.1 | saline sodium citrate |
| MES | 6.15 | 5.5-6.7 | −0.011 | 195.2 | 2-(N-morpholino)ethanesulfonic acid |

Assays, Devices, and Methods of the Invention

In one aspect, this invention provides for a kit for the accurate and rapid detection of disease causing microbes in a sample by the detection of microbial components of which correlate to the presence of the microbe. The kit comprises: a first binding agent operatively coupled to an immobilized support; and a second binding agent operatively coupled to one or more pH indicating moieties wherein the first and second binding agents bind with sufficient specificity to the microbial component to permit detection of that component which correlates to the presence of the microbe in the sample.

In the kits and/or devices according to this invention, the binding agents may be lyophilized. Lyophilized is a dehydration process typically used to preserve or increase the stability of or, alternatively, increase the stability at ambient temperature of compounds, antibodies, and other perishable materials. Lyophilization also makes the material more convenient for transport. Lyopholization works by freezing the material and then reducing the surrounding pressure to allow the frozen water in the material to sublime directly from the solid phase to the gas phase. Reconstitution of lyophilized agents can be performed with a suitable solution, saline or water, for example, prior to use. Methods for lyophilization are well known in the art (See, for example, US publication 2004/0081588 and US publication 2005/0226893 both of which are incorporated herein by reference in their entirety).

It is contemplated that kits and devices described herein can contain controls that can increase the accuracy of detection. In certain embodiments, such controls will reduce the number of false positives in the assay. One such control includes the use of a non-binding agent operatively coupled to an immobilized support. In this control, when sample containing a microbial component is added, the microbial component should not bind to the agent immobilized on the solid support and thus, no color change would be observed after the wash. Another control may be a control non-microbial component composition for the detection of non-specific binding of the first or second binding agent. Such non-microbial component composition may be a sample that is known to not contain microbial component or, alternatively, a solution with a compound or molecule with no specific binding activity to the binding agents in the device or kit. Another control includes a control microbial component or microbial component mimic composition for the detection of specific binding of the first or second binding agent. A microbial component mimic is one that may be non-toxic but still retain binding activity to the binding agents of the assay.

In the devices according to this invention, the controls can be done in compartments, preferably compartments of the same device as the assay compartments. For example, one such control compartment may comprise: a control first non-binding agent operatively coupled to an immobilized support; and a control second binding agent operatively coupled to pH indicating moieties. Another control compartment includes a microbial component binding agent operatively coupled to an immobilized support; and a microbial component non-binding agent operatively coupled to pH indicating moieties. It is contemplated that the use of controls in the kits and devices described herein will increase the accuracy of such device or kit. In certain embodiments the accuracy is about 95% or about 96%. Preferably the accuracy is about 97 to about 99.9%, more preferably, about 98 to about 99.9%, and even more preferably, 99 to about 99.9%.

Certain aspects of the invention relate to a method for accurately and rapidly detecting the presence or absence of microbial components in a sample said method comprising:

providing an assay device having an assay compartment for conducting the assay wherein said assay compartment comprises a first binding agent operatively coupled to an immobilized support; and a second binding agent operatively coupled to one or more pH indicating moieties wherein the first and second binding agents bind with sufficient specificity to a microbial component so as to permit detection of the microbe in the sample and further wherein the second binding agent is not operatively coupled to the immobilized support to which the first binding agent is bound;

adding the sample to the assay compartment of the assay device;

incubating the assay compartment under conditions sufficient to permit binding of the first and second binding agent to at least a portion of any microbial component present;

washing the assay compartment one or more times with a first inert solution under conditions which remove any of the second binding agent not bound to the microbial component;

adding a second inert solution wherein the pH of the second inert solution is one which allows the visible detection of the presence or absence of pH indicating moities in the assay;

and correlating the color or lack thereof with the presence or absence of a microbial component in a sample.

In a related embodiment, the pH of said inert solution is one in which said pH indicating moieties are colorful. pH buffers useful in the instant invention are those described previously. In one embodiment, the pH of the first inert solution is at a physiological pH and the pH of the second inert solution is at a pH that produces a visible color in the pH indicating moiety. In a preferred embodiment, the pH of the first solution is one that fosters the specific binding of the binding agents and microbial components in the assay. In another embodiment, the first inert and second inert solution are the same, or, alternatively, are at the same pH. In some instances, it is preferred that the assay be conducted at a pH in which the pH indicators are a color visible by the naked eye. By conducting the assay in this way, it is possible to determine where the pH indicators are in the assay, i.e. whether they have been washed out during the washing steps, or whether they remain bound to the immobilized support.

As in the kits and devices of this invention, the methods described herein also include methods in which the first or second binding agent is lyophilized. It is contemplated that lyophilization of components of the assays and kits in this invention will allow for increased stability in the stored devices and kits. Such increased stability may be particularly useful in remote and isolated regions of the world where such detection of toxins is vital to the everyday health of individuals in those regions.

In one embodiment, the method also comprises contacting the sample with the control compartments of the device according to this invention and correlating the absence of a visible color in said control compartments with specific binding in the assay. In a related embodiment, the method also comprises contacting a control non-microbial composition with an assay compartment for the detection of non-specific binding of the first or second microbial component-binding agent and correlating the absence of a visible color in said assay compartments with the absence of non-specific binding in the assay. In another related embodiment, the method also comprises contacting a control microbial component or microbial component mimic composition with an assay compartment for the detection of specific binding of the first or second toxin-binding agent and correlating the presence of a color in said assay compartment with specific binding in the assay. It is contemplated that the use of such controls will increase the accuracy of methods according to this invention. In certain embodiments the accuracy is about 95% or about 96%. Preferably the accuracy is about 97 to about 99.9%, more preferably, about 98 to about 99.9%, and even more preferably, 99 to about 99.9%.

A binding agent is a protein, antibody, peptide, nucleic acid, or compound that is capable of binding to and detecting the presence of a microbial component in a sample. Microbial components are molecules produced by microorganisms, including bacteria, viruses and fungi. Microbial toxins are important virulence determinants responsible for microbial pathogenicity and/or evasion of the host immune response. Some bacterial toxins, such as *Botulinum* neurotoxins, are the most potent natural toxins known.

Pathogenic toxins and/or microbial components which can be detected by methods, kits and devices of this invention include, but are not limited to, toxins, such as exotoxins and/or endotoxins produced by *Streptococcus* spp., including *Streptococcus pneumoniae, Streptococcus pyogenes* and *Streptococcus Sanguis; Salmonella* spp., including *Salmonella enteritidis; Campylobacter* spp., including *Campylobacter jejuni; Escherichia* spp., including *E. coli; Clostridia* spp., including *Clostridium difficile* and *Clostridium botulinum; Staphylococcus* spp., including *Staphylococcus aureus;*

*Shigella* spp., including *Shigella dysenteriae; Pseudomonas* spp., including *Pseudomonas aeruginosa; Bordatella* spp., including *Bordatella pertussis; Listeria* spp., including *Listeria monocytogenes; Vibrio cholerae; Yersinia* spp., including *Yersinia enterocolitica; Legionella* spp., including *Legionella pneumophilia; Bacillus* spp., including *Bacillus anthracis; Helicobacter* spp.; *Corynebacteria* spp.; *Actinobacillus* spp.; *Aeromonas* spp.; *Bacteroides* spp. including *Bacteroides fragilis; Neisseria* spp, including *N. meningitidis; Moraxella* spp., such as *Moravella catarrhalis* and *Pasteurella* spp. Also included are protozoal toxins, such as toxins produced by *Entameoba histolytica* and *Acanthameoba*; and parasitic toxins. In one embodiment, the toxin is one produced by *Vibrio cholerae*.

Methods, kits and devices of this invention can also be used to detect viral toxins, such as a toxin produced by rotavirus, human immunodeficiency virus, influenza virus, polio virus, vesicular stomatitis virus, vaccinia virus, adenovirus, piavirus, togaviruses (such as sindbis and semlikifores viruses), paramyxoviruses, papillomaviruses. Toxins which can be detected using the methods, kits and devices of this invention include viroporin molecules produced by any of these viruses. Other toxins which can be detected include influenza M2 protein, HIV Vpu and gp41 proteins, picornavirus 3A protein, togavirus 6K protein, respiratory syncitial virus SH protein, coronavirus D3 protein and adenovirus E5 protein.

Binding agents for toxins are known in the art and, in many cases, are commercially available. Some examples of binding agents include proteins that are known receptors for the toxins, antibodies with binding affinity for the toxin, and compounds that specifically bind the toxin.

Methods of making or screening binding agents are well known in the art. Methods for the production of antibodies that bind microbial toxins can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antiben depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., American Type Culture Collection (ATTC) and Life Technologies., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of this invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) Biolnvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134.

Methods of in silico molecule or compound design that allow for the design of binding agents to microbial toxins are well known in the art, see generally Kapetanovic (2008) Chem Biol. Interact., 171(2):165-76. Briefly, the atomic coordinates of the three-dimensional structure are input into a computer so that images of the structure and various parameters are shown on the display. The design typically involves positioning a three-dimensional structure to the three-dimensional structure of the target molecule. The positioning can be controlled by the user with assistance from a computer's graphic interface, and can be further guided by a computer algorithm looking for potential good matches. Positioning also involves moving either or both of the three-dimensional structures around at any dimension.

Then, the resultant data are input into a virtual compound and/or agent library. Since a virtual library is contained in a virtual screening software such as DOCK-4 (Kuntz, UCSF), the above-described data may be input into such a software. Candidate agents may be searched for, using a three-dimensional structure database of virtual or non-virtual drug candidate compounds, such as MDDR (Prous Science, Spain).

A candidate agent is found to be able to bind to a microbial toxin if a desired interaction between the candidate agent and either or both is found. The interaction can be quantitative, e.g, strength of interaction and/or number of interaction sites, or qualitative, e.g., interaction or lack of interaction. The output of the method, accordingly, can be quantitative or qualitative. The potential binding effect (i.e., interaction or association) of an agent such as a small molecule compound may be analyzed prior to its actual synthesis and testing by the use of computer modeling techniques. If the theoretical structure of the given compound suggests insufficient interaction and association between it and microbial toxin, synthesis and testing of the agent can be obviated. However, if computer modeling indicates a strong interaction, the agent can then be synthesized and tested for its ability to bind using various methods such as in vitro or in vivo experiments.

Commercial computer programs are also available for in silico design. Examples include, without limitation, GRID (Oxford University, Oxford, UK), MCSS (Molecular Simulations, Burlington, Mass.), AUTODOCK (Scripps Research Institute, La Jolla, Calif.), DOCK (University of California, San Francisco, Calif.), GLIDE (Schrodinger Inc.), FlexX (Tripos Inc.) and GOLD (Cambridge Crystallographic Data Centre).

Immobilized support as used herein is meant to refer to a solid support in which a binding agent can be operatively coupled to. Non-limiting examples include columns, assay plates, and beads such as sepharose, agarose, or metallic beads, for example. The immobilized support determines the format of the analysis, and may be chosen freely among suitable such supports. For example, the microtiter plates used as standard for known immunoassays may advantageously also be used in the methods, kits and devices of the invention. Microtiter plates for use as support may for reasons of commercial availability have 48, 96 or 384 wells. Examples of other suitable solid supports, on which the assay method of the invention may be performed, are compact discs comprising microfluidic channel structures; protein array chips; membranes, e g nitrocellulose or PVDF membranes; microparticles, e g paramagnetic or non-paramagnetic beads; pin structures; stick structures, e g dip sticks; sensor surfaces for biosensors, e g sensor chip surfaces for use in surface plasmon resonance instruments; and cell surfaces. Immobilization of the first toxin binding agent to such solid supports or substrates may be performed using covalent or non-covalent coupling procedures available for the substrate chosen, and is well within the grasp of the skilled person.

The binding agent can be immobilized, for example, by insolubilizing a capture reagent before the assay procedure, such as by adsorption of the capture reagent to a water-insoluble matrix or surface (See U.S. Pat. No. 3,720,760). The binding agent can also be insolubilized by non-covalent or covalent coupling to a water-insoluble matrix or surface, for example, using glutaraldehyde or carbodiimide cross-linking, with or without prior activation of the assay surface with, for example, nitric acid and a reducing agent. See, for example U.S. Pat. No. 3,645,852 and Rotmans et al., 1983, J. Immunol. Methods, 57:87-98.

A large number of other different immobilization techniques have been used and are well known in the fields of solid phase immunoassays, nucleic acid hybridization assays and immobilized enzymes, see, for example, Hermanson, Greg, T. Bioconjugate Techniques. Academic Press, New York. 1995, 785 pp; Hermanson, G. T., Mallia, A. K. & Smith, P. K. Immobilized Affinity Ligand Techniques. Academic Press, New York, 1992, 454 pp; and Avidin-Biotin Chemistry: A Handbook. D. Savage, G. Mattson, S. Desai, G. Nielander, S. Morgansen & E. Conklin, Pierce Chemical Company, Rockford Ill., 1992, 467 pp.

In certain embodiments the pH indicating moieties are selected from heptamethoxy red and hexamethoxy red or a combination thereof. In another embodiment, the pH indicating moieties are a derivative of heptamethoxy red or hexamethoxy red. Other examples of pH indicator moieties useful in the invention include xylenol blue (p-xylenolsulfonephthalein), bromocresol purple (5',5"-dibromo-o-cresolsulfonephthalein), bromocresol green (tetrabromo-m-cresolsulfonephthalein), o-cresol red (o-cresolsulfonephthalein), m-cresol purple, thymol blue, o-cresolphthalein, thymolphthalein, crystal violet, malachite green, phenolphthalein, phenol red, bromothymol blue (3',3"-dibromothymolsulfonephthalein), p-naphtholbenzein (4-[alpha-(4-hydroxy-1-naphthyl)benzylidene]-1(4H)-naphthalenone), neutral red (3-amino-7-dimethylamino-2-methylphenazine chloride), pentamethoxy red, hexamethoxy red and heptamethoxy red, and combinations thereof The pH indicating moieties can be conjugated to binding agents by methods known in the art and are described in, for example, U.S. Pat. No. 5,350,674, U.S. Pat. No. 5,191,066 and U.S. Patent Application 2006/0246523 all of which are incorporated herein by reference in their entirety. It is contemplated that multiple pH indicating moieties can be operatively coupled to the binding agent. Such multimerization would allow for increased sensitivity.

It is contemplated that pH indicating moieties can be conjugated as described herein and used in any established assay for detection. Such assays are commonly known and include ELISAs, western blots, protein purification assays, and protein quantification assays.

Throughout the disclosure, reference is made to prior publications, each of which is herein incorporated by reference in its entirety.

We claim:

1. A kit for the accurate and rapid detection of disease causing microbes in a sample by the detection of microbial components of which correlate to the presence of the microbe, said kit comprising:
   a first binding agent coupled to an immobilized support; and
   a second binding agent coupled to one or more pH indicating moieties wherein said pH indicating moieties are optically clear at physiological pH and colored at non-physiological pH; and
   an inert pH buffered solution wherein the pH of the solution is one which allows for a rapid color induction to visibly detect the presence or absence of pH indicating moieties
   wherein the first and second binding agents bind with specificity to the microbial component to permit detection of that component which correlates to the presence of the microbe in the sample.

2. The kit of claim 1 wherein the first binding agent is lyophilized.

3. The kit of claim 1 wherein the second binding agent is lyophilized.

4. The kit of claim 1 further comprising a control microbial component non-binding agent coupled to an immobilized support.

5. The kit of claim 1 further comprising a control non-microbial component composition for the detection of non-specific binding of the first or second binding agent.

6. The kit of claim 1 further comprising a control microbial component or microbial component mimic for the detection of specific binding of the first or second binding agent.

7. The kit of claim 1 wherein the microbial component is a toxin.

8. A device for the accurate and rapid detection of a microbial component which correlates to the presence of a disease causing microbe in a sample comprising:
   an assay device having one or more assay compartments wherein each assay compartment comprises:
      a first binding agent coupled to an immobilized support; and
      a second binding agent coupled to one or more pH indicating moieties wherein said pH indicating moieties are optically clear at physiological pH and colored at non-physiological pH and are selected from the group consisting of hexamethoxy red and heptamethoxy red or a combination thereof; and
      an inert pH buffered solution wherein the pH of the solution is one which allows the rapid color induction to visibly detect the presence of pH indicating moieties;
      wherein the first and second binding agents bind with specificity to the microbial component to permit detection of the microbe in the sample and further
      wherein the second binding agent is not coupled to the immobilized support to which the first binding agent is bound.

9. The device of claim 8 further comprising control compartments.

10. The device of claim 9 wherein each control compartment comprises:
    a control microbial component non-binding agent coupled to an immobilized support; and
    a microbial component-binding agent coupled to pH indicating moieties.

11. The device of claim 9 wherein each control compartment comprises:
    a microbial component binding agent coupled to an immobilized support; and
    a microbial component non-binding agent coupled to pH indicating moieties.

12. The device of claim 8 wherein the first binding agent is lyophilized.

13. The device of claim 8 wherein the second binding agent is lyophilized.

14. A method for accurately and rapidly detecting the presence or absence of microbial components in a sample said method comprising:
    providing an assay device having an assay compartment for conducting the assay wherein said assay compartment comprises a first binding agent coupled to an immobilized support; and a second binding agent coupled to one or more pH indicating moieties wherein said pH indicating moieties are optically clear at physiological pH and colored at non-physiological pH and are selected from the group consisting of hexamethoxy red and heptamethoxy red or a combination thereof wherein the first and second binding agents bind with specificity to a microbial component so as to permit detection of the microbe in the sample and further wherein the second binding agent is not coupled to the immobilized support to which the first binding agent is bound;
    adding the sample to the assay compartment of the assay device;
    incubating the assay compartment under conditions sufficient to permit binding of the first and second binding agent to at least a portion of any microbial component present;
    washing the assay compartment one or more times with a first inert solution under conditions which remove any of the second binding agent not bound to the microbial component;
    adding a second inert solution wherein the pH of the second inert solution is one which causes rapid color induction upon addition of said solution thereby allowing the visible detection of the presence or absence of pH indicating moieties in the assay;
    and correlating the color or lack thereof with the presence or absence of a microbial component in a sample.

15. The method of claim 14 wherein the first binding agent is lyophilized.

16. The method of claim 14 wherein the second binding agent is lyophilized.

17. The method of claim 14 wherein the microbial component is a toxin.

* * * * *